(12) United States Patent
Hawkins

(10) Patent No.: US 8,978,493 B2
(45) Date of Patent: Mar. 17, 2015

(54) CONDUIT LENGTH ADJUSTMENT APPARATUS AND METHOD

(75) Inventor: Phillip J. Hawkins, Irwin, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 576 days.

(21) Appl. No.: 13/559,764

(22) Filed: Jul. 27, 2012

(65) Prior Publication Data

US 2014/0026687 A1  Jan. 30, 2014

(51) Int. Cl.
*G01N 17/04* (2006.01)
*G01N 35/00* (2006.01)

(52) U.S. Cl.
CPC ............ *G01N 35/0099* (2013.01); *G01N 17/04* (2013.01)
USPC ...................................................... 73/865.8

(58) Field of Classification Search
CPC ........................... G01N 17/04; G01N 35/0099
See application file for complete search history.

(56) References Cited

U.S. PATENT DOCUMENTS

| 4,580,426 | A | | 4/1986 | Zafred |
| 5,392,626 | A | | 2/1995 | Blezard et al. |
| 6,003,607 | A | * | 12/1999 | Hagen et al. ................. 166/381 |
| 6,429,649 | B1 | | 8/2002 | Boynton et al. |
| 6,606,920 | B2 | | 8/2003 | Hawkins et al. |
| 7,096,699 | B2 | | 8/2006 | Bryan |

OTHER PUBLICATIONS

International Search Report for PCT/US2013/051632 dated Dec. 12, 2013 (Form PCT/ISA/210).
Written Opinion of the International Searching Authority for PCT/US2013/051632 dated Dec. 12, 2013 (Form PCT/ISA/237).

\* cited by examiner

*Primary Examiner* — Paul West
(74) *Attorney, Agent, or Firm* — Richard J. Coldren; Westinghouse Electric Company LLC

(57) ABSTRACT

A conduit length adjustment apparatus having first and second housings each having a member structured to engage the respective housing with a first conduit. A housing movement device is connected between the first and second housings and configured to change a distance between the first and second housings. Selective operation of the members and housing movement device causes the first conduit to move into or out of a second conduit.

19 Claims, 4 Drawing Sheets

CONDUIT LENGTH ADJUSTMENT APPARATUS AND METHOD

BACKGROUND

1. Field

The present invention relates generally to conduit length adjustment apparatuses for steam generators and more particularly to a conduit length adjustment apparatus between a probe pusher and a steam generator tube sheet in a steam generator.

2. Related Art

Pressurized water nuclear reactors employ steam generators to isolate and place a radioactive coolant, flowing in a primary circulation loop, in heat exchange relationship with a secondary fluid flowing in a secondary circulation loop. Steam is generated from the secondary fluid. The steam generally is employed to drive a turbine to perform work, e.g., an electric generator. In the primary loop the reactor coolant is heated by the nuclear reactions occurring in the reactor core and circulated through a hot piping leg to a hemispherical bowl shaped portion of the primary side of the steam generator generally known as the channel head. The channel head is separated, by a partition across its diameter, into inlet and outlet plenums, which are covered by a tube sheet through which the terminating ends of U-shaped heat exchanger tubes are fastened. Each of the U-shaped heat exchanger tubes originate in a bore in the tube sheet passing from the inlet plenum of the channel head and terminate in a bore in the tube sheet that communicates with the outlet plenum of the channel head. A cylindrically shaped secondary side of the steam generator is disposed around and over the tube sheet and the U-shaped heat transfer tubes. Hot, radioactive water from the reactor core circulates through the primary side of the steam generator, while non-radioactive water is introduced into the secondary side. The tube sheet and heat exchanger tubes hydraulically isolate but thermally connect the primary side to the secondary side. Hot radioactive water from the primary side flows through the interior of these heat exchanger tubes while the exterior of these tubes come into contact with the non-radioactive water in the secondary side in order to generate nonradioactive steam.

In the secondary side of the steam generator exterior portions of the U-shaped heat exchanger tubes are supported by and extend through bores present in a plurality of horizontally supported plates that are vertically spaced along the elongated length of the tubes. Small annual spaces are present between the heat exchanger tubes and the bores in the support plates, and the tube sheet, which are known in the art as "crevice regions." Such crevice regions provide only a very limited flow path for the feed water that circulates throughout the secondary side of the steam generator, which causes "dry boiling" to occur wherein the feed water boils so rapidly that these regions can actually dry out during operation of the steam generator. This chronic drying out causes impurities in the water to precipitate and collect in these crevice regions. These precipitates ultimately create sludge and other debris that promotes the occurrence of corrosion in the crevice regions which, if not repaired, can ultimately cause the tube to crack and to allow radioactive water from the primary side to contaminate the non-radioactive water in the secondary side of the steam generator.

Eddy current probe systems are employed to monitor the extent of degradation in the walls of the heat exchanger tubes that result from corrosion. One such system is described in U.S. Pat. No. 5,174,165 issued Dec. 29, 1992 to the assignee hereof. One of the services performed at a nuclear power plant is eddy current inspection of the steam generator tubing using such a system. The inspection involves insertion and removal of various configurations of eddy current probes in the high radiation and contaminated area of a nuclear steam generator. Minimizing personal time and equipment near the manway opening through which access to the interior of the steam generator is obtained (generally referred to as the steam generator platform) is highly desirable due to the elevated radiation level in that area. Typically the probes are attached to a long flexible piece of tubing (poly) and driven with a probe pusher through a flexible conduit to an area of interest or the entire length of the steam generated tube. One end of the flexible conduit is generally fixed to the probe pusher while the opposite end is attached to and positioned under the steam generator tube with a robotic manipulator.

A problem during eddy current inspection is that the amount of conduit in the steam generator needs to be increased or decreased as the robotic manipulator moves to various tube locations. This task is typically accomplished by manually adding or removing sections of the flexible conduit on the steam generator platform, which is a source of radiation exposure time for the field service operators. One method that does not require conduit length change is described in U.S. Pat. No. 6,606,920 issued Aug. 19, 2003 to the assignee hereof U.S. Pat. No. 6,606,920 describes a system in which the probe pusher is mounted to a drive system which enables both the probe pusher and the conduit to reposition during eddy current inspection. While the arrangement described in U.S. Pat. No. 6,606,920 is effective, the amount of working space required to translate the probe pusher is not available at many power plants.

It is an object of this invention to overcome these difficulties.

SUMMARY

These and other objects are achieved by a conduit length adjustment apparatus including a first conduit, a second conduit, and a conduit length adjustment device. The conduit length adjustment device includes a first housing including a first member structured to selectively engage the first housing with the first conduit, a second housing attached to the second conduit and including a second member structured to selectively engage the second housing with the first conduit, and a housing movement device coupled to the first housing and the second housing. An operation of the housing movement device changes a distance between the first housing and the second housing. When the first housing is engaged with the first conduit, the second housing is disengaged from the first conduit, and the housing movement device is operated, a portion of the first conduit moves into or out of the second conduit.

The first member and the second member may be bladders. The housing movement device may be a piston. The piston may be annular and disposed around the first conduit. The first housing and the second housing may be annular and disposed around the first conduit. In one embodiment, when the first housing is disengaged from the first conduit, the second housing is engaged with the first conduit, and the housing movement device is operated, the first conduit does not move with respect to the second conduit. In one embodiment, when the first housing is engaged with the first conduit and the second housing is engaged with the first conduit, the first conduit does not move with respect to the second conduit. In one embodiment, the conduit length adjustment device includes a first port configured to receive pressure to operate the first member to selectively engage the first housing with the first conduit, a second port configured to receive pressure to operate the second member to selectively engage the second housing with the first conduit, a third port configured to receive pressure to operate the housing movement device to increase the distance between the first housing and the second housing, and a fourth port configured to receive pressure to operate the housing movement to decrease the distance between the first housing and the second housing, wherein the first port, the second port, the third port, and the fourth port are axially aligned. The first conduit and the second conduit may include flexible tubing.

Features and utilities of the present inventive concept may also be realized by a steam generator tube inspection system including a robotic manipulator configured to move a conduit to a selected steam generator tube, a probe pusher connected to the conduit and configured to feed a probe through the conduit to the selected steam generator tube, and a conduit length adjustment apparatus. The conduit length adjustment apparatus is disposed along the conduit between the robotic manipulator and the probe pusher. The conduit length adjustment apparatus includes a first conduit, a second conduit, and a conduit length adjustment device. The conduit length adjustment device includes a first housing including a first member structured to selectively engage the first housing with the first conduit, a second housing attached to the second conduit and including a second member structured to selectively engage the second housing with the first conduit, and a housing movement device coupled to the first housing and the second housing. An operation of the housing movement device changes a distance between the first housing and the second housing. When the first housing is engaged with the first conduit, the second housing is disengaged from the first conduit, and the housing movement device is operated, a portion of the first conduit moves into or out of the second conduit.

Features and utilities of the present inventive concept may also be realized by a method for adjusting a length of a conduit in a steam generator tube inspection system. The method includes providing a conduit length adjustment apparatus between a probe pusher and a steam generator tube sheet. The conduit length adjustment apparatus includes a first housing including a first member structured to selectively engage the first housing with the first conduit, a second housing attached to the second conduit and including a second member structured to selectively engage the second housing with the first conduit, and a housing movement device coupled to the first housing and the second housing. An operation of the housing movement device changes a distance between the first housing and the second housing. The method further includes engaging the first housing with the first conduit, disengaging the second housing from the first conduit, and while the first housing is engaged with the first conduit and the second housing is disengaged from the first conduit, operating the housing movement device to move the first conduit into or out of the second conduit.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
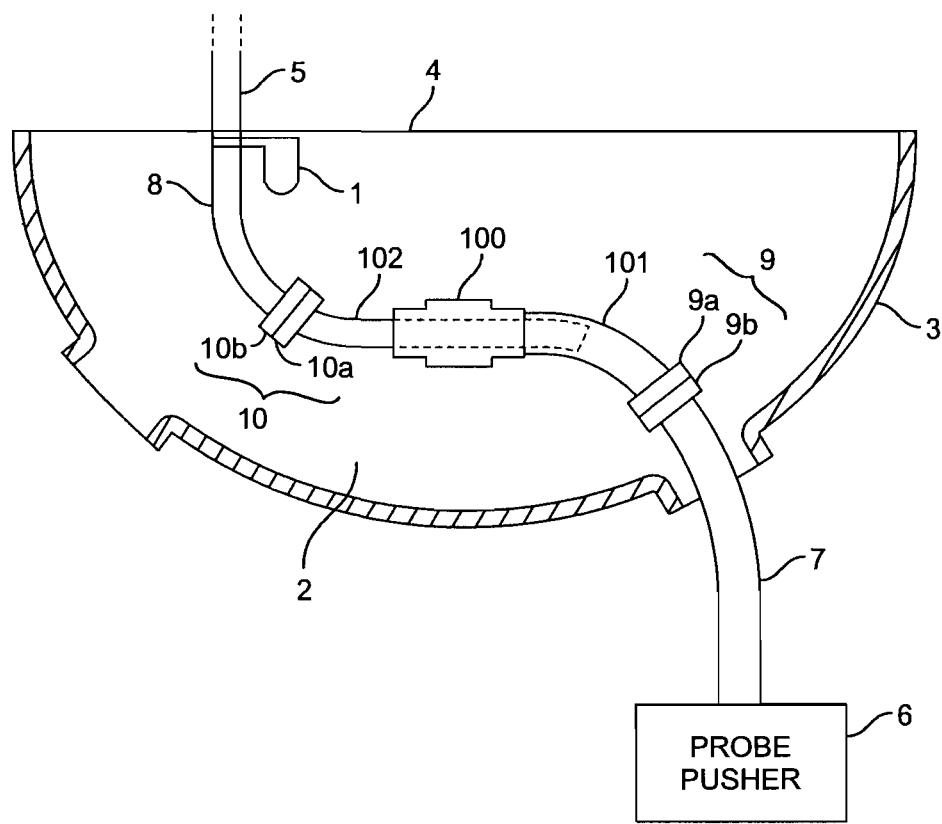
FIG. 1 is a cross sectional view of the inlet side of the steam generator channel head with the conduit length adjustment apparatus installed between the probe pusher and steam generator tube according to an embodiment of the invention.

FIG. 1 is a cross sectional view of the inlet side of a steam generator channel head 2 with a conduit length adjustment device 100 installed between a probe pusher 6 and a steam generator tube 5.

The channel head 2 area is defined by the channel head housing 3 and the steam generator tube sheet 4. The steam generator tubes, such as steam generator tube 5, are accessed through the steam generator tube sheet 4. A robotic manipulator 1 is in the channel head 2 and is used to position the conduit 8 near the steam generator tube sheet 4 at a location of a steam generator tube to be inspected. As illustrated in FIG. 1, the conduit 8 is positioned at the location of the steam generator tube 5. The probe pusher 6 pushes an eddy current probe (not shown) through the conduits 7, 8, 101, and 102 and into the steam generator tube 5 to be inspected.

As illustrated in FIG. 1, the conduit between the probe pusher 6 and steam generator sheet 4 is composed of four conduits 7, 8, 101, and 102. One end of conduit 7 is connected to probe pusher 6 and the other end of conduit 7 is connected to conduit 101 by connector 9. One end of conduit 101 is connected to conduit 7 by connector 9 and the other end of conduit 101 is connected to the conduit length adjustment device 100. One end of conduit 102 is inserted through the conduit length adjustment device 100 and into conduit 101. The other end of conduit 102 is connected to conduit 8 by connector 10. One end of conduit 8 is connected to conduit 102 by connector 10 and the other end of conduit 8 is disposed near the steam generator tube sheet 4 and is manipulated by the robotic manipulator 1 so as to be positioned by the steam generator tube 5 to be inspected. Although connectors 9 and 10 are illustrated as two part connectors with connector portions 9a, 9b, 10a, and 10b, it is contemplated that connectors 9 and 10 may be any type of connector suitable for connecting the conduits. Conduits 7, 8, 101, and 102 may each be flexible or rigid conduits.

Although FIG. 1 illustrates four conduits 7, 8, 101, and 102 between the probe pusher 6 and the steam generator tube sheet 4, it is appreciated that the present invention is not limited thereto. Any number of conduits greater than two may be included between the probe pusher 6 and the steam generator tube sheet 4. Additionally, conduits 7 and 8 may be omitted and conduits 101 and 102 may be directly connect to probe pusher 6 and steam generator tube sheet 4 without any intervening conduits.

The conduit length adjustment device 100 is used to move conduit 102 into conduit 101 and move conduit 102 out of conduit 101. Moving conduit 102 into conduit 101 shortens the length of conduit between probe pusher 6 and steam generator tube sheet 4 and moving conduit 102 out of conduit 101 increases the length of conduit between probe pusher 6 and steam generator tube sheet 4.

Although FIG. 1 illustrates the conduit length adjustment device 100 inside the channel head 2, the present invention is not limited thereto. The conduit length adjustment device 100 may be located anywhere between probe pusher 6 and steam generator tube sheet 4. Additionally, it is contemplated to be within the scope of the invention that any number of conduit length adjustment devices 100 may be located between probe pusher 6 and steam generator tube sheet 4. Furthermore, it is contemplated that the conduit length adjustment device 100 may be reversed such that the conduit 102 connects to conduit 7 or probe pusher 6 and conduit 101 connects to conduit 8 or robotic manipulator 1 while remaining within the scope of the invention.

Figure 2:
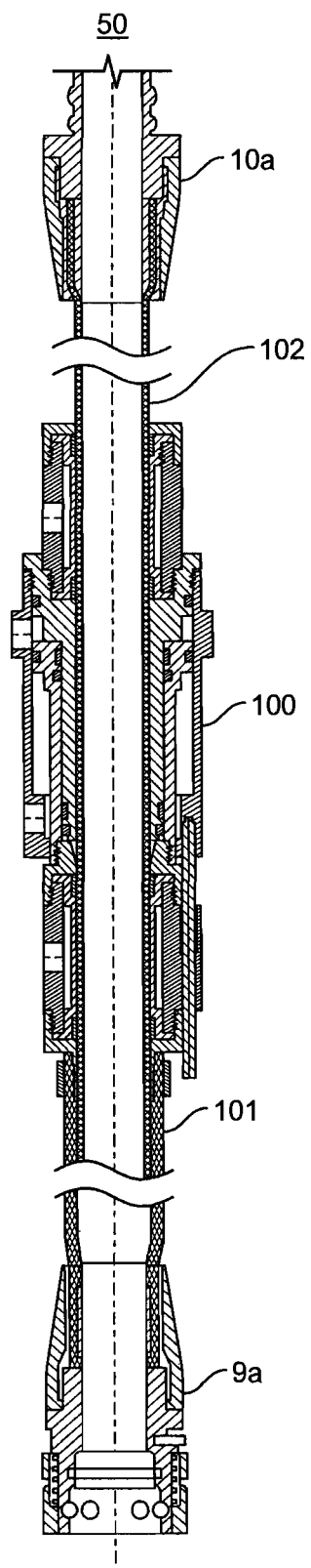
FIG. 2 is a cross sectional view of a conduit length adjustment assembly according to an embodiment of the invention.

FIG. 2 is a cross sectional view of a conduit length adjustment assembly 50. The conduit length adjustment assembly 50 includes connector portions 9a and 10a, conduits 101 and 102, and conduit length adjustment device 100. In the example embodiment illustrated in FIG. 2, connector portion 9a is a male connector portion and connector portion 10a is a female connector portion. The conduit length adjustment assembly 50 may be inserted as a segment of conduit between the probe pusher 6 and the steam generator tube sheet 4. The conduit length adjustment assembly 50 may also connect directly to the probe pusher 6 and steam generator tube sheet 4 and serve as the entire conduit between the probe pusher 6 and the steam generator tube sheet 4.

Figure 3:
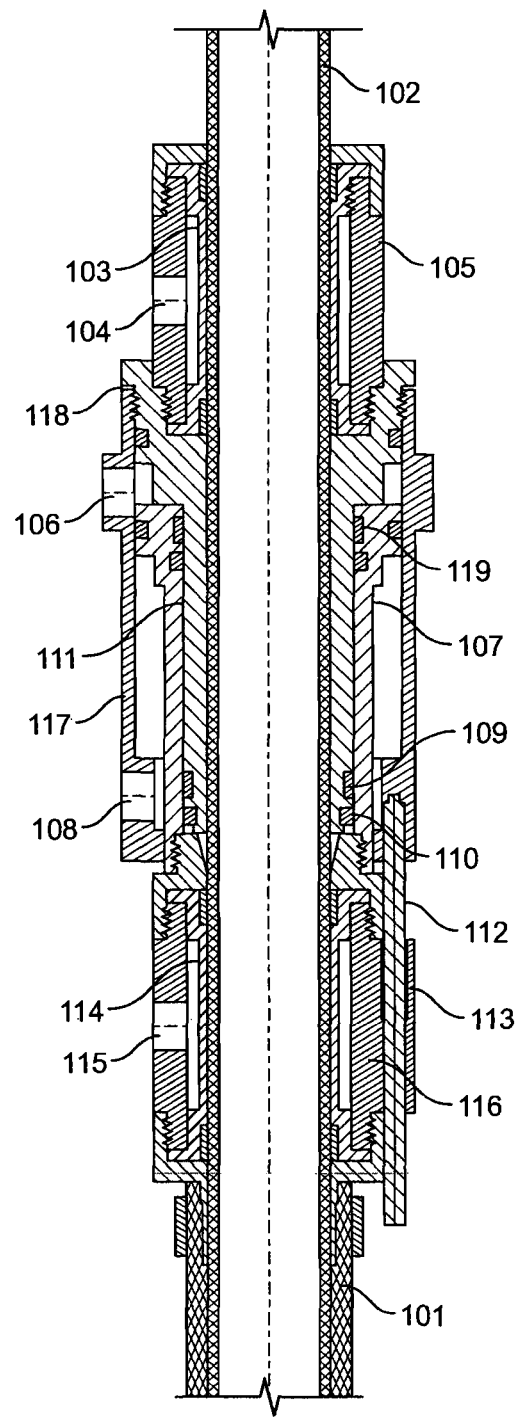
FIG. 3 is a cross sectional view of the conduit length adjustment apparatus according to an embodiment of the invention.

FIG. 3 is a cross sectional view of the conduit length adjustment device 100 according to an embodiment of the present invention. As illustrated in FIG. 3, one end of the conduit length adjustment device 100 is connected to conduit 101. Conduit 102 is inserted into the other end of the conduit length adjustment device 100 and continues into conduit 101. The conduit length adjustment device 100 is used to move conduit 102 into conduit 101 or move conduit 102 out of conduit 101, as described in more detail below.

The conduit length adjustment device 100 includes a first bladder housing 105 which includes a first port 104 in fluid communication with a first bladder 103. When pressure is applied to the first port 104, the first bladder 103 engages the first bladder housing 105 with conduit 102 so as to hold the first bladder housing 105 at the engaged location on the conduit 102. The conduit length adjustment device 100 also includes a second bladder housing 116 which includes a second port 115 and a second bladder 114. When a pressure is applied to the second port 115, the second bladder 114 engages the second bladder housing 116 with the conduit 102 so as to hold the second bladder housing 116 at the engaged location on the conduit 102. As employed herein, the statement that a housing is engaged with a conduit shall mean that the positions of the housing and the conduit are fixed with respect to each other. When a housing is disengaged from a conduit, it shall mean that the housing and the conduit can move with respect to each other.

In the exemplary embodiment illustrated in FIG. 3, the first and second bladders 103 and 114 can additionally provide a leak tight pressure boundary. While the exemplary embodiment illustrated in FIG. 3 includes bladders to engage, it is contemplated that any suitable member may be used to selectively engage the first and second housings 105 and 116 with the conduit 102. For example and without limitation, solenoids may be used to selectively engage the first and second housings 105 and 116 with the conduit 102.

The conduit length adjustment device 100 also includes a piston 107. In the example embodiment illustrated in FIG. 3, the piston 107 is annular and arranged around the conduit 101. Additionally, the first bladder housing 105 and second bladder housing 116 are annular and arranged around conduit 101. This arrangement permits a high translation force within a minimum amount of space. However, the present invention is not limited to this arrangement and other arrangements of the piston 107 and housings 105 and 107 are contemplated to be within the scope of the invention.

Pressure is applied to the piston through port 106 or 108 so as to move the piston 107 in the desired direction. The piston 107 slides along inner housing 111 and the piston's 107 sliding motion is guided by split bushings 109 and 119. Wiper 110 helps to prevent contamination of the piston 107 and split bushings 109 and 119.

One end of the piston 107 is connected to the second bladder housing 116 so that the movement of the piston 107 changes the distance between the first bladder housing 105 and the second bladder housing 116. By controlling the engagement and disengagement of the first bladder 103 and the second bladder 114 and the operation of the piston 107, moving conduit 102 into conduit 101 and moving conduit 102 out of conduit 101 can be controlled. Although the exemplary embodiment shown in FIG. 3 includes a piston 107, it is contemplated that any suitable housing movement device may be used to change the distance between the first housing 105 and the second housing 116.

The following are exemplary operations of the conduit length adjustment device 100. To move the conduit 102 out of the conduit 101, the first bladder 103 is engaged with the first conduit 102, the second bladder 114 is disengaged from conduit 102, and the piston 107 is operated to increase the distance between the first bladder housing 105 and the second bladder housing 116. The second bladder 114 is then disengaged with the conduit 102, the first bladder 103 is disengaged from the first conduit 102, and the piston 107 is operated to decrease the distance between the first bladder housing 105. By repeating this process of engaging and disengaging the first and second bladders 103 and 114 and operating the piston 107, the conduit 102 can be moved out of conduit 101 by a desired amount, thus increasing the length of the conduit between the probe pusher 6 and the steam generator tube sheet 4 by the desired amount. After the length is adjusted by the desired amount, both the first bladder 103 and the second bladder 114 can be engaged to secure the conduit 102 in place. In an example embodiment, the sequencing of engagement and disengagement of the first and second bladders 103 and 114, along with operation of the piston 107, is controlled by an electronic controller, such as, for example and without limitation, a computer, so as to provide efficient operation and prevent the simultaneous release of both the first and second bladders 103 and 114.

Similarly, to move the conduit 102 into the conduit 101, the second bladder 114 is engaged with the conduit 102, then the first bladder 103 is disengaged from the conduit 102, and the piston 107 is operated to increase the distance between the first bladder housing 105 and the second bladder housing 116. The first bladder 103 is then engaged with conduit 102 and the second bladder 114 is disengaged from conduit 102, then the piston 107 is operated to decrease the distance between the first bladder housing 105 and the second bladder housing 116. By repeating this process of engaging and disengaging the first and second bladders 103 and 114, and operating the piston 107, the conduit 102 can be moved into conduit 101 by a desired amount, thus decreasing the length of the conduit between the probe pusher 6 and the steam generator tube sheet 4 by a desired amount. After the length is adjusted by the desired amount, both the first bladder 103 and the second bladder 114 can be engaged to secure the conduit 102 in place.

The conduit length adjustment device 100 also includes bushing 113 and shaft 112. Shaft 112 is slidably connected to hushing 113 and outer housing 117 so to as keep port 115 axially aligned with ports 106 and 108. The conduit length adjustment device 100 can also include shim 118. A size of the shim 118 can be adjusted so as to change the amount threads of outer housing 117 engage with threads of inner housing 111, and thereby axially align port 104 with ports 106 and 108. Axially aligning ports 104, 106, 108, and 115 permits an efficient connection to the ports.

Figure 4:
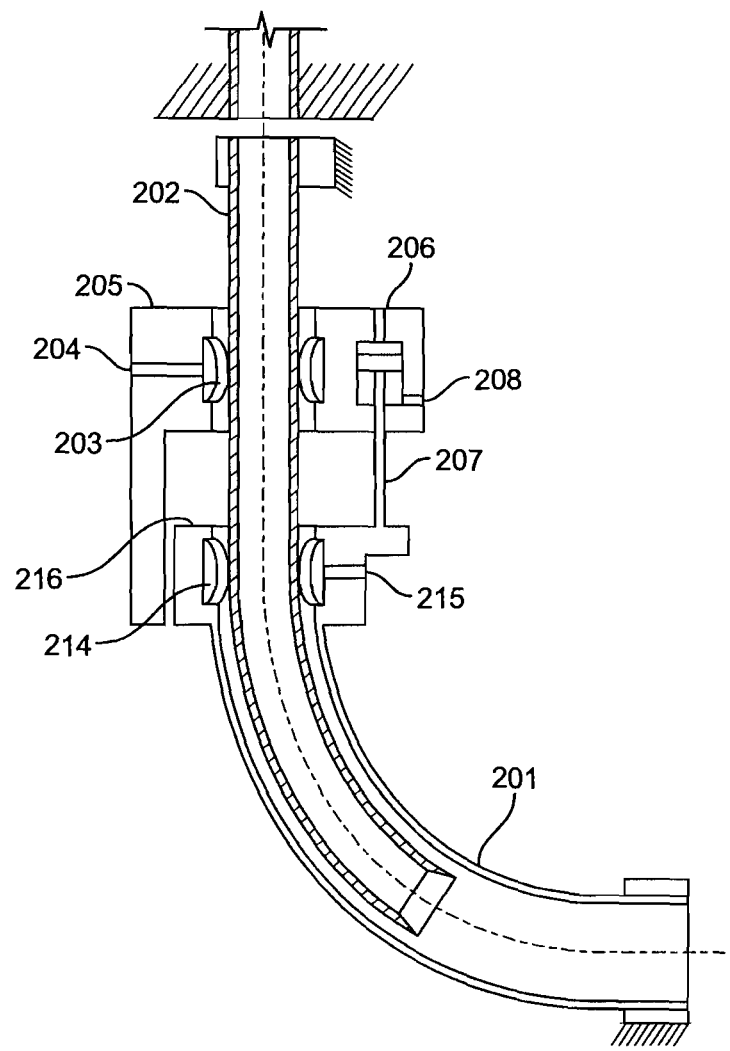
FIG. 4 is a cross sectional view of a conduit length adjustment apparatus according to another embodiment of the invention.

FIG. 4 illustrates a conduit length adjustment apparatus according to another exemplary embodiment of the invention. The conduit length adjustment apparatus includes a first housing 205 and second housing 216. The first housing 205 includes a first port 204 and a first bladder 203. The first housing 205 also includes a third port 206 and fourth port 208 which receive pressure to operate the piston 207. The second housing 216 includes the second bladder 214 and second port 215.

The conduit length adjustment apparatus illustrated in FIG. 4 moves conduit 202 into and out of conduit 201 by selectively engaging and disengaging the first and second bladders 203 and 214 and operating piston 207, similar to the operation of the conduit length adjustment apparatus described above with respect to FIGS. 2 and 3. However, the conduit length adjustment apparatus illustrated in FIG. 4 differs in that the first housing 205, second housing 216, and piston are not annular. Additionally, in the embodiment illustrated in FIG. 4, conduit 202 includes a chamfered end which allows easy passage a probe into conduit 202. It is contemplated that a chamfered end can readily be incorporated into conduit 102 in the embodiment illustrated in FIG. 1 while remaining within the scope of the invention.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A conduit length adjustment apparatus comprising:
   a first conduit;
   a second conduit, wherein the first conduit is configured to move into and out of the second conduit; and
   a conduit length adjustment device including:
      a first housing including a first member structured to selectively engage the first housing with the first conduit;
      a second housing attached to the second conduit and including a second member structured to selectively engage the second housing with the first conduit, wherein a portion of the first conduit is disposed inside the second conduit; and
      a housing movement device that is remotely operated and coupled to the first housing and the second housing, wherein an operation of the housing movement device changes a distance between the first housing and the second housing to lengthen or shorten an overall length from a first end of the first conduit to a second end of the second conduit,
   wherein when the first housing is engaged with the first conduit, the second housing is disengaged from the first conduit, and the housing movement device is operated, a portion of the first conduit moves into or out of the second conduit,
   wherein the first and second housings are disposed outside of the first and second conduits.

2. The conduit length adjustment apparatus of claim 1, wherein the housing movement device is a piston.

3. The conduit length adjustment apparatus of claim 2, wherein the piston is annular and disposed around the first conduit.

4. The conduit length adjustment apparatus of claim 1, wherein when the first housing is disengaged from the first conduit, the second housing is engaged with the first conduit, and the housing movement device is operated, the first conduit does not move with respect to the second conduit.

5. The conduit length adjustment apparatus of claim 1, wherein when the first housing is engaged with the first conduit and the second housing is engaged with the first conduit, the first conduit does not move with respect to the second conduit.

6. The conduit length adjustment apparatus of claim 1, wherein the conduit length adjustment device further comprises:
   a first port configured to receive pressure to operate the first member to selectively engage the first housing with the first conduit;
   a second port configured to receive pressure to operate the second member to selectively engage the second housing with the first conduit;
   a third port configured to receive pressure to operate the housing movement device to increase the distance between the first housing and the second housing; and
   a fourth port configured to receive pressure to operate the housing movement to decrease the distance between the first housing and the second housing.

7. The conduit length adjustment apparatus of claim 1, wherein the first conduit and the second conduit include flexible tubing.

8. A conduit length adjustment apparatus comprising:
   a first conduit;
   a second conduit, wherein the first conduit is configured to move into and out of the second conduit; and
   a conduit length adjustment device including:
      a first housing including a first member structured to selectively engage the first housing with the first conduit;
      a second housing attached to the second conduit and including a second member structured to selectively engage the second housing with the first conduit, wherein a portion of the first conduit is disposed inside the second conduit; and
      a housing movement device coupled to the first housing and the second housing, wherein an operation of the housing movement device changes a distance between the first housing and the second housing,
   wherein when the first housing is engaged with the first conduit, the second housing is disengaged from the first conduit, and the housing movement device is operated, a portion of the first conduit moves into or out of the second conduit, and
   wherein the first member and the second member are bladders.

9. A conduit length adjustment apparatus comprising:
   a first conduit;
   a second conduit, wherein the first conduit is configured to move into and out of the second conduit; and
   a conduit length adjustment device including:
      a first housing including a first member structured to selectively engage the first housing with the first conduit;
      a second housing attached to the second conduit and including a second member structured to selectively engage the second housing with the first conduit, wherein a portion of the first conduit is disposed inside the second conduit; and
a housing movement device coupled to the first housing and the second housing, wherein an operation of the housing movement device changes a distance between the first housing and the second housing,
wherein when the first housing is engaged with the first conduit, the second housing is disengaged from the first conduit, and the housing movement device is operated, a portion of the first conduit moves into or out of the second conduit,
wherein the housing movement device is a piston,
wherein the piston is annular and disposed around the first conduit, and
wherein the first housing and the second housing are annular and disposed around the first conduit.

10. A steam generator tube inspection system comprising:
a robotic manipulator configured to move a conduit to a selected steam generator tube;
a probe pusher connected to the conduit and configured to feed a probe through the conduit to the selected steam generator tube; and
a conduit length adjustment apparatus disposed along the conduit between the robotic manipulator and the probe pusher, the conduit length adjustment apparatus comprising:
a first conduit;
a second conduit, wherein the first conduit is configured to move into and out of the second conduit; and
a conduit length adjustment device including:
a first housing including a first member structured to selectively engage the first housing with the first conduit;
a second housing attached to the second conduit and including a second member structured to selectively engage the second housing with the first conduit, wherein a portion of the first conduit is disposed inside the second conduit; and
a housing movement device coupled to the first housing and the second housing, wherein an operation of the housing movement device changes a distance between the first housing and the second housing,
wherein when the first housing is engaged with the first conduit, the second housing is disengaged from the first conduit, and the housing movement device is operated, a portion of the first conduit moves into or out of the second conduit.

11. The steam generator tube inspection system of claim 10, wherein the first member and the second member are bladders.

12. The steam generator tube inspection system of claim 10, wherein the housing movement device is a piston.

13. The steam generator tube inspection system of claim 12, wherein the piston is annular and disposed around the first conduit.

14. The steam generator tube inspection system of claim 13, wherein the first housing and the second housing are annular and disposed around the first conduit.

15. The steam generator tube inspection system of claim 10, wherein when the first housing is disengaged from the first conduit, the second housing is engaged with the first conduit, and the housing movement device is operated, the first conduit does not move with respect to the second conduit.

16. The steam generator tube inspection system of claim 10, wherein when the first housing is engaged with the first conduit and the second housing is engaged with the first conduit, the first conduit does not move with respect to the second conduit.

17. The steam generator tube inspection system of claim 10, wherein the conduit length adjustment device further comprises:
a first port configured to receive pressure to operate the first member to selectively engage the first housing with the first conduit;
a second port configured to receive pressure to operate the second member to selectively engage the second housing with the first conduit;
a third port configured to receive pressure to operate the housing movement device to increase the distance between the first housing and the second housing; and
a fourth port configured to receive pressure to operate the housing movement to decrease the distance between the first housing and the second housing.

18. The steam generator tube inspection system of claim 10, wherein the first conduit and the second conduit include flexible tubing.

19. A method for adjusting a length of a conduit in a steam generator tube inspection system, the method comprising:
providing a conduit length adjustment apparatus between a probe pusher and a steam generator tube sheet, the conduit length adjustment apparatus including a first housing including a first member structured to selectively engage the first housing with the first conduit, a second housing attached to the second conduit and including a second member structured to selectively engage the second housing with the first conduit, wherein a portion of the first conduit is disposed inside the second conduit, and a housing movement device coupled to the first housing and the second housing, wherein an operation of the housing movement device changes a distance between the first housing and the second housing;
engaging the first housing with the first conduit;
disengaging the second housing from the first conduit; and
while the first housing is engaged with the first conduit and the second housing is disengaged from the first conduit, operating the housing movement device to move the first conduit into or out of the second conduit.

* * * * *